Figure 1A:
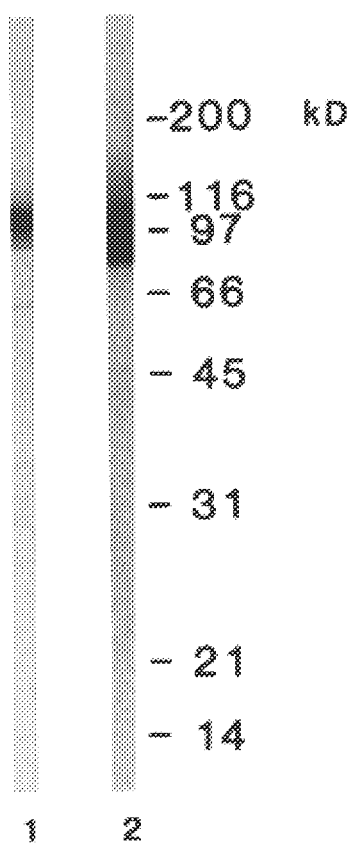

United States Patent [19]
Clarke et al.

[11] Patent Number: 5,814,320
[45] Date of Patent: Sep. 29, 1998

[54] *EIMERIA TENELLA* POLYPEPTIDE AND VACCINE CONTAINING SAME

[75] Inventors: Lorraine Elizabeth Clarke, Cumnor; Fiona Margaret Tomley, Cambridge, both of United Kingdom; Rein Dijkema, ML Oss; Arno Vermeulen, HH Cuyk, both of Netherlands

[73] Assignee: Akzo Nobel N.V., Arnhem, Netherlands

[21] Appl. No.: 473,468

[22] Filed: Jun. 7, 1995

Related U.S. Application Data

[62] Division of Ser. No. 500,162, Mar. 27, 1990, Pat. No. 5,677,438.

[30] Foreign Application Priority Data

Mar. 28, 1989 [EP] European Pat. Off. .............. 89303032

[51] Int. Cl.⁶ ................. A61K 39/00; A61K 39/012; C12P 21/06
[52] U.S. Cl. ..................... 424/267.1; 424/184.1; 424/185.1; 424/271.1; 530/350; 435/69.1; 435/69.3
[58] Field of Search .................. 424/267.1, 184.1, 424/185.1, 271.1; 530/350, 326, 352

[56] References Cited

U.S. PATENT DOCUMENTS

| | | | |
|---|---|---|---|
| 4,639,372 | 1/1987 | Murray et al. | 424/88 |
| 4,650,676 | 3/1987 | Schenkel et al. | 424/88 |
| 4,710,377 | 12/1987 | Schenkel et al. | 424/88 |
| 5,279,960 | 1/1994 | Anderson et al. | 435/243 |

FOREIGN PATENT DOCUMENTS 0164176  12/1985  European Pat. Off. .

OTHER PUBLICATIONS

L.E. Clarke et al., *Molecular and Biochemical Parasitology*, 22 (1987) 79–87.

M.C. Jenkins et al., *Experimental Parasitology*, 66:96–107 (1988).

*Primary Examiner*—Hazel F. Sidberry
*Attorney, Agent, or Firm*—Mary E. Gormley

[57] ABSTRACT

The invention is concerned with a protein having the immunological properties of *Eimeria tenella* which is reactive with a monoclonal antibody E. TEN 11P-2 raised against *E. tenella* sporozoites.

The invention also relates to polypeptide fragments of this protein which can be used for immunization against *E. tenella*. These proteins and polypeptides can be prepared by isolation from *E. tenella*, by chemical synthesis or by recombinant DNA methods using the polynucleotides described herein or related sequences.

5 Claims, 17 Drawing Sheets

```
  1 AAGCTTAAGCAAGACTACAGTGAAGCGTATACACATGATGAGTCTTGCCGGAGCCTTG
 61 CTAAAACAAACGAGTTGCTAGTCGATTGCATCATATACACCTCATACTAACCAGTCCA
121 GATAATGAACATTCGCAATCAAACTTACAACCAAACTTTTGAAGCATTGTCCGAACAAGA
181 ACTAATTGCCTCTGAAGGATCGAATGCAAGCAAACATAACTATTCCTGTGTGCGAA
241 TCGACATATGCACACAGCGCAGAGACGTCACTTTAAACATGCTTGGAGAAACTTGC
301 TTTTCCATGTCTAATGCAAAAAGCAAGTTGGAATAACACTCTCAATATCTAGCTACGG
361 ATATTCTACACTATCAGAGCCCGATACGTGTGTGAAGGCGAGCGAAGCTGTTCACTCGTG
421 GCTTCAGCTGAAAAATAATGACAATGCGCTAGACGGGGAGTCGAAGGTGTCTGTAT
481 GCTGTCGTGAGTAAACCACAGGAAATCGCTTAATAAGAGCTGAAGAAAGCAATAACAAT
541 ATACGTGATCTGCCTGACTTGCAGATCCCGGAACTACCAGTCATTGCGCGCCAG
601 CCGCGAGTACGCACTAGCAGGAGACCCTTGCGAGCCATCGACTTCAATGTCTCACAGTA
661 GAATTCGGTTAGTTTCAAAACATATTGTTTTGTTAGTCATTTCTAATCTCCTATT
                                               M  A  P  L  P
721 CTTCATCTTTTTACCCAGTTCGCCTTTCTTGCATCATTCCGCAATGCGCCCTTCCTC
     R  R  R  L  A  P  C  R  A  L  S  L  L  V  G  L  L  A  A  S
781 GGCGAAGGCTAGCGCCCTGCAGGCCATTATCATTGCGTTGCTGCTTGCCGCCAAGTT
     F  A  F  S  S  L  Q  P  [------------
841 TTGCTTCTTTCTTCTTTACAGCCAGTTCGTCATTCATGGTTATAATGGCAAGTGGCTCCG
```

FIG. 6A

901 TTGCAAACTTGTGTGCCCATTGCTGCTATTCCAACTGAGAGTGGTTCTGGCCATGGCGAAC

961 AGTGCCTTTGACGGTGGCTTCCTGATCAATGCTGTCACAGAAGTCTTAGCAGTTGCAAAG

1021 ATAGGGTCATATAGTTAGTGCACCAGTGTCACCTGGGTGTTTTAATTTGTAAGGGTCGAG (INTRON 1)

1081 AGGTTGGGCTTCAATGCCAGCATCGTTTGCCTCGCGGATCTCGCGTAAAGGTAGCG

1141 CACGTTGTCCCCTTGTGGCTTTCCCTTGGGGTGACGAAGTTCGATTAGGCAGAAATTTTGC

1201 CGGCCACAGGCTTGAAAGGACATTACCCTCTGGGTTGATGTAGGCTGCTCTTGAAGTGATATT

1261 GCCCCTTTGTTGTTGCGTTGGCTGCTAGGTGTACAGTGTCACTTGCCGTTGCATTGCTG

1321 GCTTTCTTATGTAACGGCGTTGACTTAGCAGGCTTCATGCGAACCTGCGATGTTTGTTAT

—]G A T T S S G Q D Q V C T S L L D V M

1381 TCAGGGCAACTACCAGCTCTGGCCAGATCAGGTGTGCACAAGCCTCTTGATGTCATG

L V V D E S G S I G T S N F R K V R Q F

1441 TTGGTAGTTGATGAGTCGGGCTCCATTGGCACATCGAACTTCAGGAAGGTGCGCAGTTC

I E D F V N S M P I S P E D V R V G L I

1501 ATCGAAGACTTCGTGAATTCTATGCCGATTTCTCCAGAGGAGTTCGTGTTGGGTTAATC

FIG. 6B

```
        T F A T R S K V R W N L S D P K A T N P
1561  ACTTTGCAACCGTTCCAAAGTTGGTTGGAACCTGAGTGATCGAAGGCTACAAATCCT

S L A I S A A R S L S Y S T G V T Y T H
1621  TCCTTGGCTATATCAGCAGCTAGATCTCTAAGCTATTCAACAGGGTCACCTACAGCAT

Y G L Q D A K K L L Y D T N A G A R N N
1681  TACGGTCTTCAAGATGCAAGAAGCTGCTCTACGACACCAATGCTGAGCTAGAAATAAC

V P K L V L V M T D G A S N L P S Q T R
1741  GTACCCAAGTTGGTTTTGTCATGACTGACGGGCAAGCAATCTCCGTCTCAAAGAGA

S S A A A L R D A G A I V V V L G V G S
1801  TCTTCTGCTGCAGCCCTGCGTGATGCAGAGAGCCATGTAGTTGTCTTGGAGTGGGCTCA

G V N S S E C R S I A G C S T N C P R
1861  GGAGTCAATTCGAGTGAGTGCAGAGTATTGCTGCTGTTGCACTTCAAATTGCCCAGG

Y L Q S N W S N V T Q Q V N G I I K A A
1921  TACTTGCAGTCAAACTGTCAAAGTCACGCAGCAGTCAATGTATCATCAAGCTGCA

C K D L A K D A V C S E W S E Y G P C V
1981  TGCAAAGATCGGCAAAGATGCGGTGTGTAGCGAATGAGCGAATATGACCTTGTGTG

G E C G K E G V Q T S T R V E I S P Q K
2041  GGGGAATGTGGCAAAGAAGGGGTGCAGACTGAGTGAGATATCTCCGCAGAAG

P G S P P C P T C E A P R G R S C A E Q
2101  CCGGGGTCACCTCCTTGCCCGACATGTGAGGCACCGAGGGCCAGGTCTGTGCCGACCAG

P P G L T R T Q P C T M P V C K T D A H
2161  CCTCCGGACTTACTCGGACCGCAGCCGTGCAGATGCCAGTGTCAAAAGGATGCTCAT
```

FIG. 6C

```
        C  G  E  F  G  A  W  S  E  W  S  T  T  C  G  T  A  T  R  K
2221    TGCGGGGAGTTTGGCGCATGTCTGAGTGGAGCACTAGTGCGGAACGGCGACGAGGAAA

R  Q  R  E  G  Y  N  S  P  P  A  A  G  G  G  L  S  C  M  E
2281    AGGCAGAGGGAAGGCTACAACAGTCCACCTGCAGCCGCGGTGTGGCTTTCTTGCATGAA

Q  N  P  P  K  H  E  F  E  V  E  T  V  Q  K  S  P  C  P  V
2341    CAAAATCCGCCTAAACATGAATTCGAGGTTGAAACGGTGCAGAAATCGCCGTGCCCAGTT

Q  Q  Q  P  G  P  W  S  E  W  T  E  C  S  A  T  C  G  G  G
2401    CAGCAACAACCCGGACCCTGGAGTGAATGGACAGAGTGCTCAGCAACTGGGAGGAGGT

T  K  H  R  E  R  E  G  L  P  Q  E  G  E  L  Y  G  G  Q  T
2461    ACTAAGCATCGGGAGCGGGAGGGTTTGCCACAGGAAGGGGAACTGTACGGGGGACAGACT

L  E  Q  Q  G  I  A  V  R  E  T  A  S  C  S  E  N  P  C  P
2521    TTGGAACAACAAGGCATTGCTGTGAGGGAAACTGCTTCGTGCAGCGAGAACCCGTGCCCT

I  D  A  T  C  G  E  W  T  E  Y  S  A  C  S  R  T  C  G  G
2581    ATCGACGCAACGTGCGGAGAATGGACAGAGTACAGTGCCTCCAGAACTGCGGAGGC

G  T  Q  E  R  K  R  E  P  W  L  D  N  A  Q  H  G  G  R  T
2641    GGTACCCAAGAGAGAAGAGAGAGCCGTGGTTGGATAATGCCAACACGGGGGCCACC

C  M  E  Q  Y  P  D  G  P  I  S  V  R  E  C  N  T  Q  P  C
2701    TGCATGGAACAGTATCCTGATGGCCCATATCGTCAGGAGTGCAACACCAGCCGTGC

P  V  D  E  V  V  G  D  W  E  D  W  G  Q  C  S  E  Q  C  G
2761    CCTGTGGACGAAGTAGTTGGTGATTGGGAAGACTGGGGCCAATGCAGCGAACAGTGTGGT

G  G  K  R  T  R  N  R  G  P  S  K  Q  E  A  M  F  G  G  K
2821    GGCGGCAAGCGGACTCGTAATCGCGGCCCAAGCAAGCAAGAGGCCATGTTCGGAGGCAAG
```

FIG. 6D

FIG. 6E

```
        T  V  A  Q  Q  N  A  E  L  P  E  G  E  K  I  E  V  V  Q  E
2881    ACAGTTGCTCAACAGAATGCAGAGCTCCCTGAAGGGAGAAGATTGAGGTTGGTTCAGGAA

E  G  C  N  E  V  P  C  [---------------------------------
2941    GAAGGATGCAATGAAGTTCCATGCGGTGACCTAGCTAGTGTAGTTGAAGGCAAAGACTGTC

---------------------------------------------------------
3001    GACTCGGTGTGTTGTACCCGTGTACAAGCTTTCAGTCGAATAATAACTGTTCTGCTTTGT

------------------------------- (INTRON 2)---------------
3061    CCGGTAGTCATGCGAATTCTGACACAGTTAGTAGGCGTCTCTTGCTCACCTTCAGACTTT

---------------------------------------------------------
3121    AGAGCGAAAGCTGTTAATTAAGGCGTATAAGCTCAGCAGGGACACATTTGTTCTGGGGT

----------]G  P  C  T  L  P  F  S  E  W  T  E  C  E  S  C  S
3181    TTCTGGGCACAGGACCTGCAGCTCCCTTCAGTGAGTGACCGAGTGAGTGAGTCGTGCT

G  H  R  T  R  E  S  A  V  A  F  D  Y  T  D  R  M  C  S  G
3241    CCGGGCATAGAACCAGGAGTACAAGCTGTAGCCATTTGATTACACTGACAGAATGCAGTG

D  T  H  E  V  Q  S  C  E  E  Y  C  S  Q  N  A  G  G  A
3301    GTGACACACACGAGTACAAAGCTGTGAGAATACTGTTCCAAAATGCTGGAGGGGGTG

G  G  D  G  G  A  G  G  G  T  G  G  S  G  E  E  E  G  K  E
3361    CTGGAGGAGATGGGGGCCAGGAGGAGGACTCGAGGCTCGGAGAGGAGGAAGGAAAGG

E  S  S  G  F  P  T  A  A  V  A  G  G  V  A  G  G  V  L  A
3421    AGGAATGCAGTTGATTCCAACTGCAGCTGTAGCCGTGCCTCGGGGAGTCCTCGB

I  A  A  G  A  F  Y  G  L [-----------------------------
3481    CCATTGCTCGGGAGCTGGAGCGTTTTATGGATTGTAAGTTTTTTAGCCGAAGCTGGCC
```

```
                                                                  ( INTRON 3 )
3541  TCTTAGCCGTTAACAGCTGTTTTGGTGATCCTTCTTGTGCCTTCCTGTCTACCTTCT
3601  CAAGCTGATGGGAATGGTAGGACGCCTGATTGAGTGGTTGCCGTCAAATATTCTGGTGTG
                ]  S   G   G   S   A   A   A   A   T   E   A   G   A   E   V   M
3661  TGCTGTTACAGGAGTGGTGGAGCGGCGCTGCCACTGAAGCAGGTGCTGAAGTGATG
          T   E   A   G   T   S   N   A   A   E   V   E   K   E   S   L   I   S   A   G
3721  ACAGAAGCTGGACATCCAATGCTGCTGAGTAGAAAGAGAGCCTCATCAGTCCAGT
          E   Q   S   E   M   W   A   S   *
3781  GAACAATCAGAGATGTGGGCATCCTAAATGAAACTCGCCGCGGGTTTGAAAAGG
3841  TGGGATCTTGCATATCTGTGAACGCATCTCTGGCGCATAGCTTCTTGAACTCCCG
3901  TTGGCAAATCATTTACCAAGCATCTCTGGCGCATAGCTTCTTGAACAAGAACGGAATG
3961  TCCAACTGGGAACAGCTATATTGCGAAGTGTGGTTCAAACCAGAAGAGAGCACAGCG
4021  TCATGTGTATGTTAGGGTTGGCGCGCCCCTTTCCTTATTTATCCATTTCCTCGCCTT
4081  CATCTTTCCGCTCCTCTCTGTGCCCGTATTTTGGGTGTTATTGGTGCCTGGGGACAT
4141  GAAAGAGAGATTGCGCGTTATTTGCAGGGTGCCAGGCCATGGTAGGGTTGGATAACACTC
4201  ATTGGTGAAGCGCAAGCGCAACAGGCCACGTTTACCTCCGGTGGTCAATGGGCAGTTG
4261  GTTCTGTCATTGGTGTCTGTTCAAGGGCCGTAATGGGCAGCAGAAGCTTCTGCCA
4321  GCCACCACAATGGAAGCAACAAATAAGGGAGGTTCTGCTAACAATTGTGCTAGTCAT
```

FIG. 6F

```
4381  GATTGTAGTAGGCTCGGTTCGAAGATGAATGACGGAGCCAGCCTGAATGAAACTGA
4441  CTCTCAAAGAAGGAATTCAAGAAAATACGGTACACCATTCTCACTTTTGAGGTGCAGC
4501  TAACGAGGACTTTTTCTTAGTAACGTATGGCATCGTGGAGCAAGGAACAGTGTTTGTG
4561  TTGCATTGTGAGCACGGAGGTGTGCCTCAGAATATAGTCTGGAGTGGAAGACAT
4621  TAAGGACCCAAGAGCCCTTTATTGCTCGGGTAGAATTCAATGTGTCTGGCATGTATCTT
4681  CGTGGACTTTTTGTCGTTATATCTACTCTAAAGTGAGTGAATGGTTGGACGCATTAAA
4741  AAGTAATTGCCTTCCCGTGAGCCAAATATTTCTGGTCTGAGGGGTGTGAGCTCTC
4801  TTTTTGCGTCGTGGGCTAGCCACTGCACACGGCCAGCCTTAACGCATGAAGTCCTCTG
4861  AAACAGTCGCACTAGCACCTCTGAAGGCCCTAACGCACCCAATAGCTTTCCTTAAATT
4921  TCTTTTGAGAGCCTAGGGTGGCGTTTCTTCAACTCACCCAATAGCTTTCCTTAAATT
4981  CGTGGGAATAGCCGCATTGTGAACAGTACTCGAGAAGCCAGTGTACGATATAGCGTGA
5041  TGCAGGATAGCGAAGAGTGCGTTAATGCAGCAGACTCTCAGGTTCAGTCGA
5101  GTAAAGGCCAGGTCCGTGCGAGTAAAGGTCAGTTTATTCTTCAGAGGATGCCTGAAGC
5161  GAACAGGACAAATGGTGTGTAGCAGGATCGCACTCTGCTCCGGCAGGTACCTTT
```

FIG. 6G

FIG. 6H

```
5221  CCCTTGTGGGTGAAGCATAGAAACAATGGGAAGGCTTGTACAATTTGCGATGAGAA
5281  GGTGACTCCTTGCCCGAGCCTTACTTAGTGTGGGGAATTCCAAGGAAGTGCAACTAG
5341  AGTCCGTGCAAGGTTTTGGTTAGAGGTCACCCAGAATCAAGACAGAATTCTGCGAGG
5401  TGGCTATCCCAGCAGAGTAACTATCTCTGCTTTGTTGTAGAATTGGACCAGAGGTTCA
5461  GGGGTGGGTTCTGATTAAGGCACAATAACGAGTCGGAGGGCATCTTTGCATGCT
5521  TCCAGTTGCGAAACTGTACTCTGCTTGCCTGCCCAGAAGGCAATGCTTATTACTTAAG
5581  ATAGAGGAGACTGTGACGATTAAATAAACCGGTAACGAGCAGAAGCCACAAGCACCT
5641  CTCCGAGCACGGAGGGCAGACCAGACTATTGTGCCCACGAATTCTACATTTGT
5701  GCCTTACTGTGTGGAAGGTGTGGGATTGGACGTTGCCTGACACGTTCGACTCTCAC
5761  TGTGCAGACTCCAACGGACCAACCAGTGGCTGCCTGGCTAGGTTGCTTTTAGTGAA
5821  ATGCAGAGATAGTGTTACTCTGGAGAAAAGAATGGCTAGGAGGGAGCCCCAATGATGAAATGACC
5881  CTAAAATTTAAGTATGACTTCGAGAAAAGAATGGCTAGGAGGGAGCGGCCATGGCGTGCA
5941  ATCTGCGTAGCAACTCGACCACGTCGCCCGGTCGGCGCGCCCCAAGCTT
```

```
        10          20          30          40          50          60
MAPLPRRRLA  PCRALSLLVG  LLAASFAFSS  LQPGATTSSG  QDQVCTSLLD  VMLVVDESGS 70          80          90         100         110         120
IGTSNFRKVR  QFIEDFVNSM  PISPEDVRVG  LITFATRSKV  RWNLSDPKAT  NPSLAISAAR 130         140         150         160         170         180
SLSYSTGVTY  THYGLQDAKK  LLYDTNAGAR  NNVPKLVLVM  TDGASNLPSQ  TRSSAAALRD 190         200         210         220         230         240
AGAIVVVLGV  GSGVNSSECR  SIAGCSTSNC  PRYLQSNWSN  VTQQVNGIIK  AACKDLAKDA 250         260         270         280         290         300
VCSEWSEYGP  CVGECGKEGV  QTSTRVEISP  QKPGSPPCPT  CEAPRGRSCA  EQPPGLTRTQ 310         320         330         340         350         360
PCTMPVCKTD  AHCGEFGAWS  EWSTTCGTAT  RKRQREGYNS  PPAAGGGLSC  MEQNPPKHEF 370         380         390         400         410         420
EVETVQKSPC  PVQQQPGPWS  EWTECSATCG  GGTKHREREG  LPQEGELYGG  QTLEQQGIAV 430         440         450         460         470         480
RETASCSENP  CPIDATCGEW  TEYSACSRTC  GGGTQERKRE  PWLDNAQHGG  RTCMEQYPDG 490         500         510         520         530         540
PISVRECNTQ  PCPVDEVVGD  WEDWGQCSEQ  CGGGKRTRNR  GPSKQEAMFG  GKTVAQQNAE 550         560         570         580         590         600
LPEGEKIEVV  QEEGCNEVPC  GPCTLPFSEW  TECESCSGHR  TRESAVAFDY  TDRMCSGDTH 610         620         630         640         650         660
EVQSCEEYCS  QNAGGGAGGD  GGAGGGTGGS  GEEEGKEESS  GFPTAAVAGG  VAGGVLAIAA 670         680         690         700         710         720
GAGAFYGLSG  GSAAAATEAG  AEVMTEAGTS  NAAEVEKESL  ISAGEQSEMW  AS
```

FIG. 8A

STATISTICAL ANALYSIS OF AMINO ACID CONTENT

| A | C | S | T | P | A | G | N | D | E | Q | B | Z | H |
|---|---|---|---|---|---|---|---|---|---|---|---|---|---|
| N | 38. | 68. | 50. | 44. | 67. | 86. | 23. | 23. | 64. | 36. | 0. | 0. | 7. |
| % | 5.3 | 9.6 | 7.0 | 6.2 | 9.4 | 12.1 | 3.2 | 3.2 | 9.0 | 5.1 | 0.0 | 0.0 | 1.0 |
| W | 3919. | 5921. | 5055. | 4273. | 4762. | 4907. | 2624. | 2647. | 8263. | 4613. | 0. | 0. | 960. |

| A | R | K | M | I | L | V | F | Y | W | — | X | ? | 0 |
|---|---|---|---|---|---|---|---|---|---|---|---|---|---|
| N | 36. | 23. | 11. | 16. | 36. | 45. | 13. | 13. | 13. | — | 0. | 0. | 0. |
| % | 5.1 | 3.2 | 1.5 | 2.2 | 5.1 | 6.3 | 1.8 | 1.8 | 1.8 | 0.0 | 0.0 | 0.0 | 0.0 |
| W | 5623. | 2948. | 1443. | 1811. | 4074. | 4461. | 1913. | 2121. | 2421. | 0. | 0. | 0. | 0. |

TOTAL MOLECULAR WEIGHT= 74778.

FIG. 8B

EIMERIA TENELLA POLYPEPTIDE AND VACCINE CONTAINING SAME

This is a division of application Ser. No. 07/500,162 filed Mar. 27, 1990 now U.S. Pat. No. 5,677,438.

The present invention is concerned with a protein with the immunological properties of Eimeria species and fragments thereof, DNA sequences coding for these, recombinant vectors and host organisms containing these DNA sequences as well as vaccines containing the said protein or protein fragments, or DNA coding for them.

Coccidiosis is a disease which is caused by intracellular parasites, protozoa, of the subphylum Apicomplexa and the genus Eimeria. These parasites multiply in cells which form part of the gastrointestinal tract and digestive organs.

Due to the increase in intensive production, the damage which is caused by these parasites in the poultry industry has risen alarmingly in recent decades. For example, the losses which poultry farmers in the Netherlands suffer every year run into millions of guilders; the loss in 1986 was about 13 million guilders; in the same year a loss of U.S.$ 300 million was suffered in the U.S., despite the use of coccidiostats.

The pathogens of coccidiosis in chickens can be subdivided into nine different species, i.e. *Eimeria acervulina, E. maxima, E. tenella, E. necatrix, E. brunetti, E. mitis, E. praecox, E. mivati* and *E. hagani*. However, some people doubt the existence of the last two species. All of these species have only the chicken as host and display a high degree of tissue specificity. The life cycles of the said species are, however, similar.

The species do differ in their pathogenic effect on chickens, the type of chicken also playing a role; thus, a broiler chicken will be subjected to a great deal of damage by a parasite such as *E. acervulina* or *E. maxima* because these parasitise large portions of the small intestine, where food digestion plays a major role.

During the life cycle, the Eimeria parasites pass through a number of stages. The infectious stage (the sporulating oocyst) is taken in orally and passes into the stomach of the chicken, where the wall of the cyst bursts open as a result of the grinding action. The four sporocysts, which this oocyst contains, are released and pass into the duodenum, where they are exposed to bile and digestive enzymes. As a result, an opening is made in the sporocyst wall and the sporozoites present in the sporocyst are released. These sporozoites are mobile and search for suitable host cells, epithelium cells, in order to penetrate and to reproduce. Depending on the species, this first reproduction phase lasts 20 to 48 hours and several tens to hundreds of merozoites are formed, which each again penetrate a new host cell and reproduce. After two to sometimes five of these asexual reproduction cycles, depending on the species the intracellular merozoites grow into sexual forms, the male and female gametocytes. After fertilization of the female by a male gamete, a zygote is formed which creates a cyst wall about itself. This oocyst leaves the host cell and is driven out with the faeces. If the temperature and humidity outside the chicken are relatively high and, at the same time, there is sufficient oxygen in the air, the oocyst can sporulate to the infectious stage.

Thus, no intermediate host is needed for transfer of the parasite from chicken to chicken. It is therefore conceivable that with a high degree of occupation of the available surface area the infection pressure in a chicken farm rapidly increases.

The parasite can be combatted in various ways.

In addition to using good management, coccidiosis can be controlled by using coccidiostatic agents which frequently are mixed in the feed or drinking water. However, these agents have suffered a drop in effectiveness in recent years, partly because of the high genetic capacity of the parasite to develop resistance against various combatting agents. In addition, a number of these agents leave residues in the meat which can give rise to problems on consumption.

Immunological prophylaxis would, therefore, constitute a much better combatting method. It is known that chickens which have lived through a sufficiently high infection are able to resist a subsequent contact with the same type of Eimeria. Resistance towards Eimeria can also be induced by infecting the birds several times with low doses of oocysts or with oocysts of weakened (non-pathogenic) strains. However, controlled administration to, specifically, large numbers of broiler chickens is a virtually insurmountable problem in this case. Inactivated vaccines therefore appear to be a feasable alternative solution.

An inactivated vaccine can consist of an antigen originating from the parasite, possibly with an adjuvant.

As an alternative to using antigen isolated from parasites, it is possible to use a product prepared with the aid of recombinant DNA technology, a technique which can be carried out according to known methods.

It is also possible to reproduce the antigen or parts thereof synthetically and to administer this to the birds in an immunologically recognizable and stimulating form, for example bonded to a carrier protein in the presence of an adjuvant.

Moreover, vaccination can be carried out by administering a live host organism such as a bacterium or a virus in which a gene coding for the antigen has been incorporated. This organism then ensures adequate long-term synthesis of antigen so that the immune system of the chicken is adequately stimulated.

According to the present invention a protein (named Etp100) or fragment thereof is provided which can be employed in the immunization of poultry against coccidiosis.

Said protein Etp100 can be isolated from an extract of *E. tenella* by applying said extract to a column substrate which contains the monoclonal antibody E. TEN. 11P-2, separating the adsorbed fraction of the extract from the unadsorbed fraction, and subsequently releasing the adsorbed fraction from the column substrate by methods known in the art.

The protein material obtained by this immune-chromatographic process optionally can be further purified by methods known in the art for purification of naturally derived products.

Characterization of the thus obtained protein Etp100 from *E. tenella* revealed the following properties:
a. molecular weight in SDS-PAGE of about 100 kD;
b. binding to monoclonal antibody E. TEN. 11P-2 under non-reducing conditions, but not under reducing conditions;
c. occurrence in the sporulated oocyst, sporocyst, sporozoite, first and second generation schizonts and second generation merozoite.

The 100 kD protein can suitably be isolated from sporozoites as well as from merozoites of *E. tenella* obtained from diverse sources.

Figure 5:
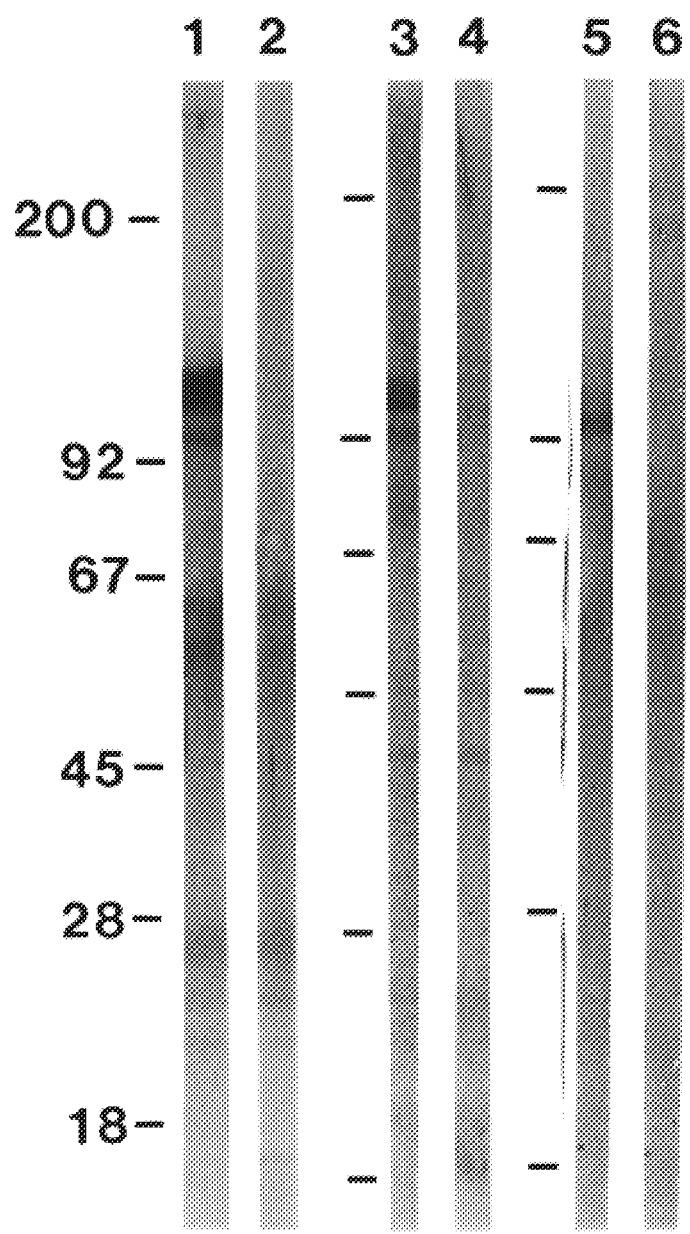

Furthermore, proteins corresponding to Etp100 can be isolated from other Eimeria species, such as from *E. maxima* and *E. acervulina*. The identification of these corresponding proteins was established by raising mouse antiserum against a fragment of the said 100 kD protein of *E. tenella* and employing the antibodies of this antiserum in a Western blot assay using *E. maxima* and *E. acervulina* sporozoites, as illustrated in FIG. 5. It was found that the proteins which can be detected in this way have molecular weights similar to Etp100 of E. tenella. The same antiserum can be used for the immune-chromatographic separation of the said E. maxima and E. acervulina proteins.

DNA sequences coding for the E. tenella protein or polypeptide fragments thereof were derived from genomic DNA as well as from complementary DNA (cDNA) derived from E. tenella mRNA as outlined by the examples to follow. These DNA sequences (as well as subsequences thereof), along with the polypeptides with Eimeria antigenicity coded for by these DNA sequences and subsequences form part of the present invention too.

It is known that for a given amino acid frequently several different codons (triplets of nucleotide bases) can code in the DNA. Thus, for example the codon for glutamic acid is GAT or GAA, etc. It is obvious that for the expression of the polypeptide with the amino acid sequence according to FIGS. 6–8 (or a polypeptide fragment thereof) use can likewise be made of a DNA with a similar alternative codon composition.

In addition, fragments of these polypeptides, which can be used for immunization of poultry against coccidiosis, also form part of the invention. Various methods are known for detecting such usable polypeptide fragments (termed epitopes) within a known or unknown amino acid sequence. On the basis of a known amino acid sequence, these epitopes can, for example, be determined experimentally with the aid of the screening techniques described in patent publications WO 84/03564 and WO 86/06487.

In addition, a number of regions of the polypeptide, with the stated amino acid sequence, can be designated epitopes on the basis of theoretical considerations and structural agreement with epitopes which are now known. The determination of these regions was based on a combination of the hydrophilicity criteria according to Hopp and Woods (PNAS USA 78: 3824–3828; 1981) and the secondary structure aspects according to Chou and Fasman (Advances in Enzymology 47: 45–148; 1987).

The following regions contain probable epitopes for antibodies (see FIG. 8): amino acid numbers about 270–300 and about 495–525.

Henceforth, the amino acid sequences ISPQKPGSP-PCPTCEAPRGRSCAEQPPGLTR and PVDEVVGDWED-WGQCSEQCGGGKRTRNRGPS as well as polypeptides containing these sequences form part of the present invention too.

T-cell epitopes which may be necessary can likewise be derived on theoretical grounds with the aid of Berzofsky's amphiphilicity criterion (Science 235: 1059–62; 1987).

For immunization against coccidiosis infection in accordance with the present invention it is also possible to use, for example, anti-idiotype antibodies or antigen-binding fragments thereof. Such antibodies are directed against the idiotype of antibodies, which, in turn, are directed against the polypeptide according to the invention. The immunogenic equivalents of the polypeptide according to the invention which have been indicated above are understood to mean, inter alia, anti-idiotype antibodies of this type.

For immunization of poultry against coccidiosis in accordance with the present invention, it is possible, either to administer the present polypeptides, fragments or immunogenic equivalents to the birds or, alternatively to administer microorganisms which by genetic manipulation using recombinant DNA or RNA techniques have acquired the ability to produce the present polypeptides or an immunogenic section or equivalent thereof, in situ.

"Subunit vaccines" is a frequently used term for the former case and the term "vector vaccines" is usually used for the latter case—we will also adopt this nomenclature here.

The subunit vaccines according to the invention in general contain the polypeptides in purified form, optionally in the presence of a pharmaceutically acceptable excipient.

The polypeptides for such applications can be prepared with the aid of known methods, such as by isolation from Eimeria, by means of recombinant DNA techniques or by peptide synthesis.

The polypeptide can optionally be covalently bonded to a non-related protein, which, for example, can be of advantage in the purification of the fusion product or help into the processing into a mature protein. Examples are β-galactosidase, protein A, prochymosine, blood clotting factor Xa, etc.

If desired, the polypeptides can also be modified in vivo or in vitro by, for example, glycosylation, amidation, carboxylation, acylation or phosphorylation.

In order to enhance their immunogenicity, these polypeptides suitably can be bound to or associated with a carrier and/or can be combined with compounds with adjuvant properties. Further, a vaccine based on these polypeptides can contain other compounds customary used in vaccines, such as stabilizers, buffers, etcetera.

In vector vaccines, the polypeptide product according to the invention is made by a genetically manipulated organism which is itself administered to the individual to be immunized and which maintains itself for some time, or even reproduces, in the body. Diverse organisms can be used as the host for this purpose, like, for example, bacteria such as Escherichia coli, Bacillus, or Salmonella, or viruses such as cowpox or fowlpox virus. With host organisms of this type, the polypeptide can express itself as a surface antigen. In this context fusion of the said polypeptide with OMP proteins or pilus proteins of Escherichia coli or synthetic provision of signal and anchor sequences which are recognized by the organism are conceivable. It is also possible that the said immunogenic polypeptide, if desired as part of a larger entity, is released inside the animal to be immunized. In all of these cases it is also possible that one or more immunogenic products will find expression which generate protection against various pathogens and/or against various antigens of a given pathogen.

Example 1

Preparation of Hybridomas
Preparation of Parasites and Fractions Thereof

E. tenella parasites were maintained and oocysts were isolated according to method3 described by Long et al. (Fol. Vet. Lat. 6: 201–217; 1976). Sporozoites were isolated and purified as described by Wisher & Rose (Parasitology 88: 515–519, 1984) with an additional nylon wool purification as described by Larsen, et al. (J.Parasitol. 70: 597–601; 1984). Second generation merozoites were isolated from chicken caecae at 96 hours post-infection by the method of Stotish & Wang (J. Parasitol. 61: 700–703; 1975) and further purified by centrifugation on a continuous 70% Percoll gradient.

Immunization and Cell Fusion

Balb/C mice were immunized with $10^6$ E. tenella sporozoites given intraperitoneally in 0.5 ml PBS (phosphate buffered saline), followed by a booster with the same dose and route four days before fusion. Six weeks after the first immunization, spleens were removed aseptically and the cells were fused with the myeloma line P3X63Ag 8.6.53. as described by Köhler and Milstein (Nature 256: 495–7; 1975) and cultured according to standard protocols.

Selection of Hybridomas

Hybridomas were selected for recognition of sporozoite antigens by using an immunofluorescence assay (IFA). Sporozoites were suspended in PBS (1–3×10$^6$ per ml) and 3 μl volumes were spotted onto 10 well glass slides (Celline), dried overnight at room temperature and stored dry at −70° C.

After thawing and fixing the slides in acetone, 25 μl of the hybridoma supernatant was spotted onto each well and allowed to incubate for 30 minutes at 37° C. Slides were rinsed in PBS and washed 3 times during 5 minutes with PBS.

Labelled rabbit-anti-mouse FITC (Nordic; fluoroisothiocyanate) was used as conjugate in 1:100 to 200 dilution, and incubated for 30 minutes at 37° C. in the presence of 0.05% Evans Blue as counter stain. After washing and rinsing the slides were mounted with 0.1 mol/l Tris-HCl; pH 9.0; 75% glycerol and assayed using a Leitz Ortholux fluorescence microscope. Hybridomas which showed to be positive in this assay were cloned further by limiting dilution, assayed again and stored in liquid nitrogen or were directly injected into pristane-primed Balb/C mice for ascites production (2.5×10$^6$ hybridoma cells per mouse i.p.). From these positive hybridomas two clones were selected which produced useful antibodies. These monoclonal antibodies indicated as E. TEN. 11P-2 and E. TEN. 10Y-2, respectively, recognized E. tenella sporozoites as well as second generation merozoites using IFA. Both fluorescence patterns were similar. And both monoclonal antibodies bound to material present in the anterior half of the zoite, possibly to a cytoplasmic protein.

Deposition of Samples

Samples of hybridoma cell lines producing these E. TEN. 11P-2 and E. TEN. 10Y-2 antibodies were deposited on Feb. 2, 1989 under No. 89020202 and No. 89020201, respectively, with the European Collection of Animal Cell Cultures at Porton Down, U.K.

Example 2

Characterization of Monoclonal Antibodies E. TEN. 11P-2 and E. TEN. 10Y-2

A. Methods

Target antigens of MoAb E. TEN. 11P-2 and E. TEN. 10Y-2 were characterized using SDS-PAGE/immunoblotting techniques as described by Vermeulen et al. (J.Exp.Med. 162: 1460–76; 1985). Briefly, 2×10$^7$ freshly excysted, nylon wool purified sporozoites were solubilized in Laemmli sample buffer (Nature 227: 680–4; 1970) without the addition of reducing agents like DTT or β-mercaptoethanol. After boiling for 5 minutes and centrifugation during 3 minutes at 18000 g the supernatant was removed, made up to 20% glycerol and loaded onto a 7 to 18% acrylamide gradient gel (or a 12% uniform gel) containing a 4% stacking gel.

After electrophoretic separation the proteins were blotted onto nitrocellulose paper (0.45 μm; Schleicher & Schüll) in 0.01 mol/l Tris; 0.079 mol/l glycine; pH 8.3 at 10 V/cm for 1 hour.

For immuno-detection the nitrocellulose strips were pretreated in 0.2% non-fat milk powder (NFMP) in PBS for 30 minutes, and incubated for 90 minutes at room temperature with tenfold diluted hybridoma supernatants in PBS; 0.05% Tween-20; 0.1% NFMP, washed extensively and incubated with anti-mouse Ig labeled with alkaline phosphatase. Bound Ig conjugate was visualized using nitro blue tetrazolium (0.33 mg/ml) and 5-bromo-4-chloro-3-indolylphosphate p-toluidine salt (0.17 mg/ml) in 100 mmol/l Tris/HCl; pH 9.5; 100 mmol/l NaCl; 5 mmol/l MgCl$_2$.

B. Results

Figure 1B:
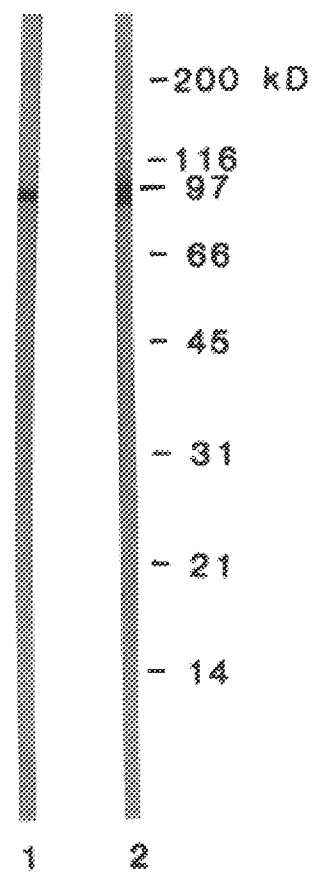

Monoclonal antibodies E. TEN. 11P-2 and E. TEN. 10Y-2 reacted on Western blots of non-reduced E. tenella sporozoite-merozoite proteins with bands of 95 to 110 kD. (FIG. 1). Bio-rad SDS-PAGE molecular weight markers were used as reference. Using specific antisera in ELISA E. TEN. 11P-2/E. TEN. 10Y-2 were characterized as being of IgG1 isotype.

Example 3

Expression of Antigen Reactive with MoAb E. TEN. 11P-2 During Development of the Parasite A. Methods Western blots were made containing lanes with comparable quantities of sporulated oocysts, purified sporocysts and purified sporozoites. Western blots were probed with monoclonal antibodies as well as chicken hyperimmune serum according to the procedure described in Example 3A.

Hyperimmune chicken serum was raised in nine chickens (7 wk. old) by oral administration of two dosages of 2×10$^4$ viable E. tenella oocysts within 4 days followed by four dosages of 10$^4$ with four day intervals. One week after the final dose all chickens were exsanguinated. The serum was pooled and anti-sporozoite titer was assayed in the immunofluorescence assay described in Example 1 as 1:1280.

B. Results

Figure 2:
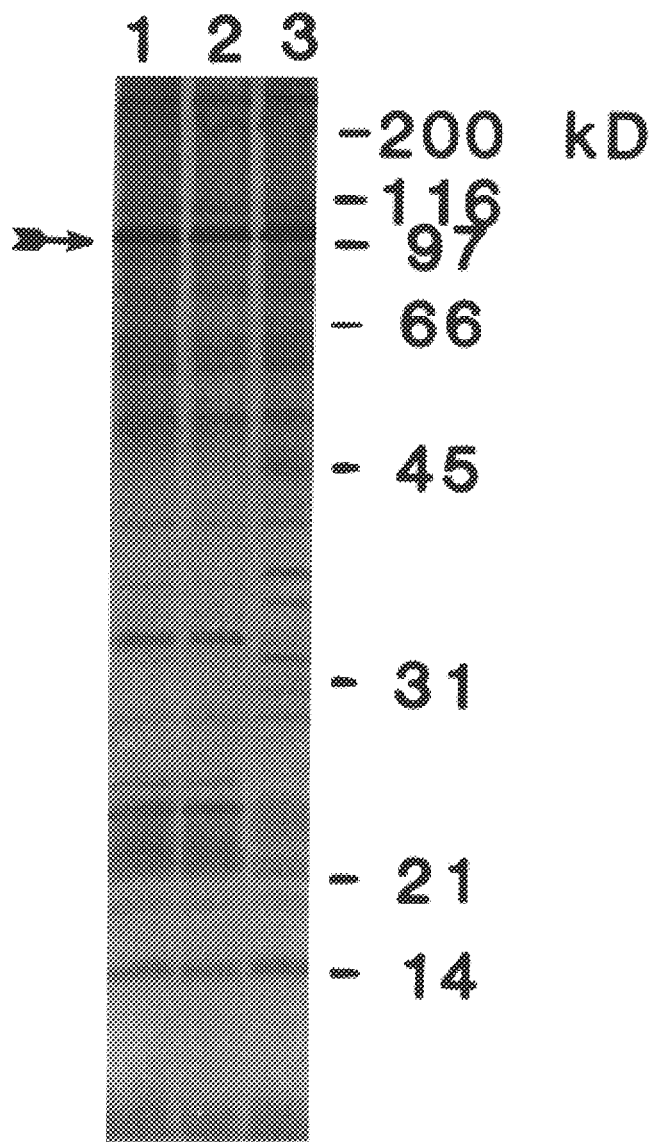

It was shown that the 95–110 kD proteins which are the target proteins of MoAb E. TEN. 11P-2 and E. TEN.10Y-2 were already present in the sporulated oocyst, and they were also expressed in the sporocyst and sporozoite stage. The 95–110 kD proteins were predominantly recognized by the hyperimmune chicken serum (FIG. 2).

Example 4

Immune-Chromatographic Purification of E. tenella Protein

Preparation of Immunoaffinity Columns

IgG, from E. TEN. 11P-2, was precipitated from ascites fluid using (NH$_4$)$_2$SO$_4$ at 50% saturation at room temperature. The material was spun down for 30 minutes at 2500 rpm in a Minifuge T (Heraeus Christ). The pellet was washed twice with 50% (NH$_4$)$_2$SO$_4$ and resuspended in half the original volume of 0.2 mol/l NaHCO$_3$, desalted over Sephadex G25 (Pharmacia PD10 columns) according to the manufacturer's instructions and coupled to CNBr-activated Sepharose (Pharmacia) overnight at 4° C. The final coupling ratio was 6.7 mg IgG per ml gel. For E. TEN. 10Y-2, IgG was concentrated and purified from ascites fluid using protein A-Sepharose (Pharmacia) according to the manufacturer's instructions. After neutralization and desalting coupling was performed as above, the final coupling ratio of the E. TEN. 10Y-2 column being 4.8 mg/ml gel.

5–7 ml of IgG-coupled Sepharose was poured into a suitable column and equilibrated in running buffer (25 mmol/l Tris/HCl; pH 8.0; 0.5 mol/l NaCl; 0.1% NP40).

Immuno-Affinity Purifications of Etp100

320×10$^6$ E. tenella sporocysts, frozen as a pellet at −70° C. were thawed and suspended in 3 ml 25 mmol/l Tris/HCl; pH 8.0; 1 mmol/l EDTA; 1 mmol/l PMSF.

The cysts were broken by vortexing in the presence of 3 g glass beads (~0.3 mm in diameter). The solution was made up to 0.1% Nonidet P40 (NP40) and incubated for 1 hr. at 0°

C. Unsolubilized material was centrifuged out at 4° C. by spinning for 15 minutes at 2000 rpm, followed by spinning for 1 hr. at 3000 rpm. The supernatant was passed through 0.22 μm filters before application to the immune-column.

5 ml of the *E. tenella* sporocyst extract was bound to E. TEN. 11P-2 and E. TEN. 10Y-2 columns at a flowrate of 0.15 ml/min. in a recirculating system overnight at ambient temperature.

After ±20 circulations the non-bound fraction was collected and kept for further analysis. The columns were washed with at least three alternating cycles of Wash 4 (0.1 mol/l acetate; 0.5 mol/l NaCl; 0.1% NP40; pH 4.0) and Wash 8 (0.1 mol/l Tris/HCl; 0.5 mol/l NaCl; 0.1% NP40; pH 8.0), flowrate 0.5 ml/min.

After two bedvolumes washing with running buffer, 4 ml of 0.1 mol/l carbonate/bicarbonate; pH 10.6; 0.1% NP40 was used for alkaline elution.

Fractions were neutralized with 1 mol/l Tris pH 8.0 and the column was re-equilibrated with running buffer. Subsequent elution was done with 0.1 mol/l glycine/HCl; 0.15 mol/l NaCl; 0.1% NP40; pH 2.6. The acidic fractions were neutralized with 1 mol/l Tris; pH 8.0.

Figure 3A:
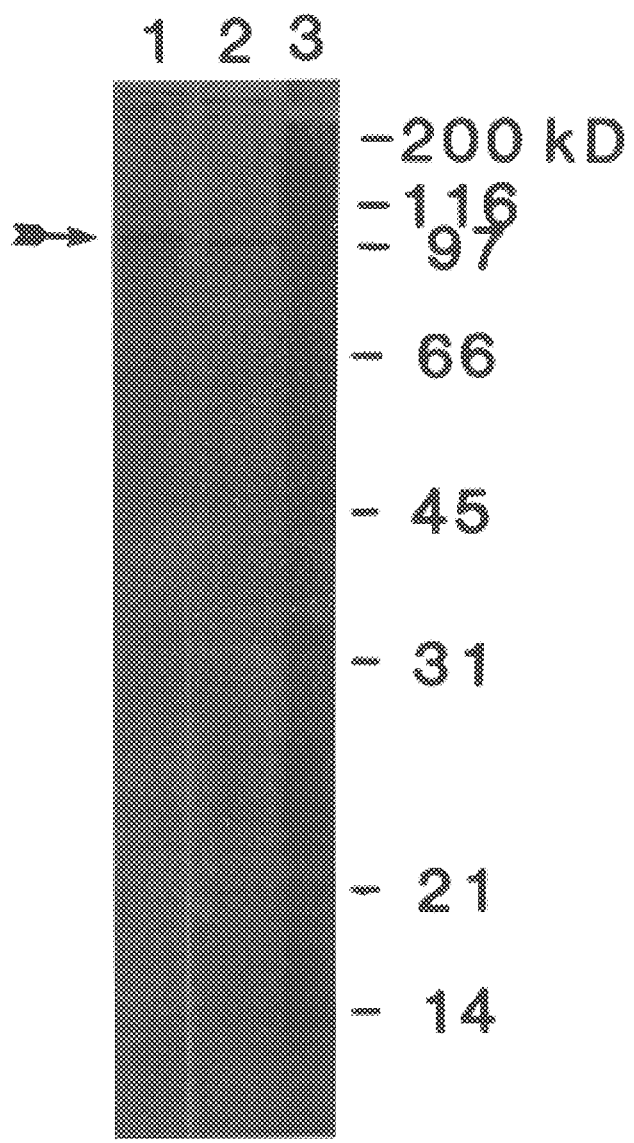
Figure 3B:
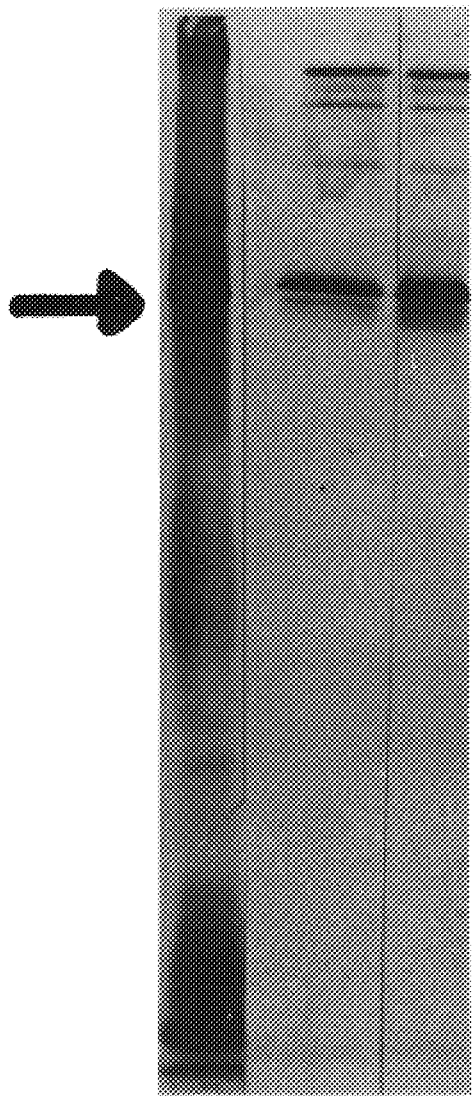

All fractions were analyzed on SDS-PAGE under non-reducing conditions and on Western blots using polyclonal rabbit anti-sporozoite serum as probing antibodies (FIG. 3). From both columns the main fraction was eluted using acidic conditions. Material eluted from the E. TEN 11P-2 column reacted positively with the E. TEN 10Y-2 MoAb (not shown).

Example 5

Preparation of cDNA Library of *E. tenella* and Immunological Screening

A. Isolation of RNA

For the isolation of RNA fully sporulated oocysts were taken up into 2.8 ml of buffer containing 10 mmol/l Tris acetate (pH 7.6); 75 mmol/l sodium acetate; 1% SDS; 2 mmol/l EDTA; 0.2 mg/ml proteinase K and 10 mmol/l vanadyl ribo-nucleoside complexes. The oocysts were broken by vortexing for 60 seconds (max) in the presence of 13 g glass beads (φ0.5 mm). 5 ml of phenol was added to the total extract and the mixture was vortexed for a further 60 seconds. After centrifuging, the aqueous layer was pipetted off and again extracted with an equal volume of a mixture of phenol, chloroform and isoamyl alcohol (25:24:1). RNA was precipitated after adding 2.5 volume ethanol and the resulting precipitate was dissolved in 800 μl of a buffer containing Tris 10 mmol/l; EDTA 0.1 mmol/l; pH 7.6, after which the product was extracted a further twice with an equal volume of phenol/chloroform/isoamyl alcohol (25:24:1) and twice with chloroform/isoamyl alcohol (24:1) and then precipitated with ethanol. PolyA$^+$-RNA was isolated by means of oligo(dT)-cellulose chromatography (Maniatis et al., ibid). Approximately 100 μg polyA$^+$-RNA was isolated from $5 \times 10^8$ oocysts.

B. cDNA Synthesis

PolyA$^+$-RNA was converted to cDNA by means of the enzyme MMLV reverse transcriptase. For this purpose 25 μg polyA$^+$-RNA was dissolved in 90 μl of water and denatured for 5 minutes at 20° C. by adding mercury methyl hydroxide to 10 mmol/l, after which β-mercaptoethanol was added to 45 mmol/l and the mixture incubated for a further 3 minutes at 20° C. The enzyme reaction was carried out in 190 μl buffer containing 4 μg oligo(dT)$_{15}$, 150 U RNAsin®, 20 mmol/l Tris (pH 7.6), 30 mmol/l KCl, 4 mmol/l dithiothreitol (DTT), 2 mmol/l MgCl$_2$, 1 mmol/l of each dNTP and 3000 U MMLV reverse transcriptase. The reaction was stopped after 1 hour incubation at 37° C. by adding 10 μl 0.5 mol/l EDTA. After extraction with an equal volume of phenol/chloroform/isoamyl alcohol (25:24:1), the RNA/DNA hybrid was precipitated by adding ammonium acetate to 2 mol/l and 2.5 volumes ethanol. The combined action of the enzymes DNA-polymerase I and RNase H results in the synthesis of the second strand. The pellet was dissolved in 960 μl of buffer containing 20 mmol/l Tris (pH 7.6), 5 mmol/l MgCl$_2$, 100 mmol/l (NH$_4$)$_2$SO$_4$, 0.6 mmol/l β-NAD, 16 U RNase H, 200 U DNA-polymerase I and 20 U DNA-ligase (*E. coli*). The incubation time was 1 hour at 12° C. and then 1 hour at 22° C., after which the reaction was stopped by adding an equal volume of phenol/chloroform/isoamyl alcohol (25:24:1) and precipitating with ethanol.

Before the cDNA was cloned in a vector suitable for this purpose it was first modified. cDNA (5 μg) was dissolved in 100 μl of buffer containing 30 mmol/l sodium acetate (pH 5.6), 50 mmol/l NaCl, 1 mmol/l ZnSO$_4$ and 21 U Mung Bean Nuclease. After incubation for 30 minutes at 37° C. the reaction was stopped by adding EDTA to 10 mmol/l and Tris to 25 mmol/l. After extraction with phenol/chloroform/isoamyl alcohol (25:24:1) the mixture was desalted on a Sephadex G50 column.

The following were added to the eluate (125 μl): Tris pH 7.6 to 50 mmol/l, EDTA to 2.5 mmol/l, DTT to 5 mmol/l, S'-adenosylmethionine to 0.5 μm and 100 U EcoRI-methylase. After incubation for 30 minutes at 37° C., the reaction was stopped by heating for 15 minutes at 65° C., after which ¹/₁₀ volume of a solution containing Tris-HCl 100 mmol/l, MgCl$_2$ 100 mmol/l and NaCl 500 mmol/l (pH 7.5) was added, and, at the same time, each dNTP to 1 mmol/l and 12.5 U Klenow DNA-polymerase. The reaction was stopped after incubating for 60 minutes at 22° C. by adding an equal volume of phenol/chloroform/isoamyl alcohol (25:24:1). Nucleic acids present in the aqueous phase were precipitated after adding 350 μl H$_2$O and 50 μl 3 mol/l sodium acetate (pH 5.6) with 500 μl isopropanol. After dissolving in 100 μl H$_2$O, the pellet was desalted on Sephadex G50 and the eluate precipitated with ethanol.

After dissolving the pellet in 24 μl H$_2$O, ligation was carried out in 50 μl by adding 2 μg EcoRI linker, Tris-HCl (pH 8.0) to 30 mmol/l, MgCl$_2$ to 10 mmol/l, dithiothreitol to 10 mmol/l, ATP to 1 mmol/l, gelatin to 0.1 mg/ml and 10 U T$_4$DNA-ligase. The reaction was stopped after 16 hours' incubation at 4° C. by heating (for 15 minutes at 70° C.) after which cutting was carried out with restriction endonuclease EcoRI in 210 μl buffer containing 100 mmol/l Tris-HCl (pH 7.6), 50 mmol/l NaCl, 10 mmol/l MgCl$_2$, 2.5 mmol/l DTT and 500 U EcoRI. After 90 minutes' incubation at 37° C., the reaction was stopped by means of extraction with an equal volume of phenol/chloroform/isoamyl alcohol (25:24:1). Nucleic acids present in the aqueous phase were precipitated with 2.5 volume ethanol after adding sodium acetate (pH 5.6) to 300 mmol/l cDNA and linkers were separated by means of a Biogel A15m column. The cDNA was precipitated with ethanol, after which the precipitate was dissolved in Tris-HCl 10 mmol/l, EDTA 0.1 mmol/l (pH 7.6). The cDNA molecules were then cloned in phage λgt11 as well as in phage λgt10, according to Huynh et al. in: DNA cloning techniques: A Practical Approach, 1984.

C. Screening of λgt11 cDNA Libraries with MoAb E. TEN. 11P-2

Proteins produced by *E. coli* Y1090$^-$ infected with λgt11 cDNA clones were immobilized on nitrocellulose filters as described (Huynh et al., ibid). The cDNA library was immuno-screened with the MoAb E. TEN. 11P-2 which resulted in a positive reaction for about 1 in $2 \times 10^5$ phage clones. The monoclonal antibodies have been purified over Protein A Sepharose®, and diluted with one volume of Tris buffer (10 mmol/l Tris-HCl; 150 mmol/l NaCl; pH 8.0) plus 0.05% Tween 20 and 10% FCS. Incubation with the filters was for two hours at 25° C. The filters were washed four times for 10 minutes with 50 ml of the above Tris buffer plus 0.05% Tween 20. The second antibody incubation with a conjugate of goat-anti-mouse-antibody and alkaline phosphatase (diluted 1:7500 with the above Tris buffer plus 0.05% Tween 20 and 10% FCS) was carried out during 30 minutes at 37° C., whereafter the filter was washed as described for the first antibody incubation. Bound alkaline phosphatases were detected after incubation during 30 minutes at room temperature in 100 mmol/l Tris-HCl; 100 mmol/l NaCl; 10 mmol/l $MgCl_2$; pH 9.6; containing 0.33 g/l nitroblue tetrazolium and 0.17 g/l 5-bromo-4-chloro-3-indolyl-phosphate.

Figure 7:
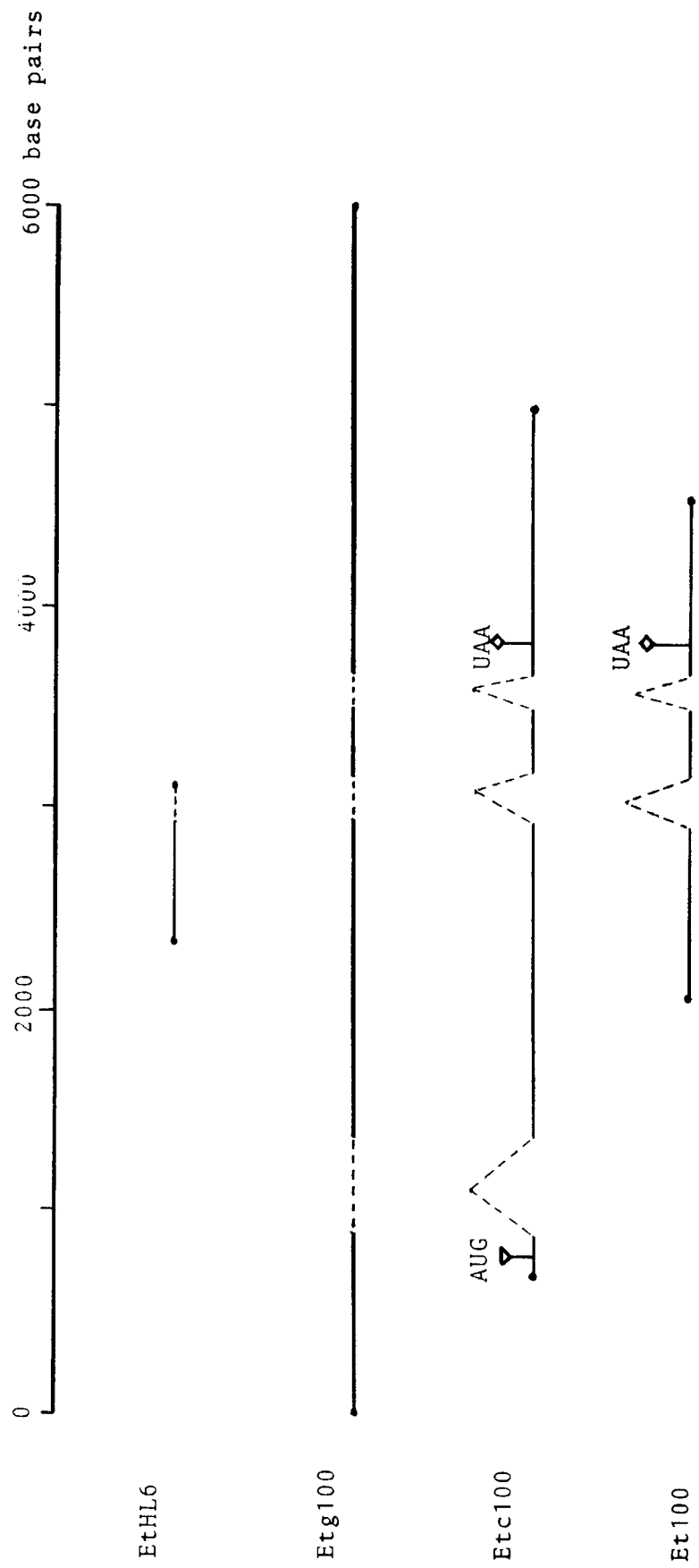

One clone which was positive in the immuno-assay was plaque purified and this clone was indicated as clone Et 100 (see also FIG. 7).

Example 6

Preparation of Genomic Library of E. tenella and Immunological Screening

A. Methods

E. coli Strains

E. coli Y1088 (supE supF strA metB trpR hsdR hsdM__tonA21 ΔlacU169 (proC::Tn5) (pMC9)), Y1089 (ΔlacU169 proA$^+$ Δlon araD139 strA hfla150 (chr::Tn10) (pMC9)) and Y1090 (ΔlacU169 proA$^+$ Δlon araD139 strA supF (trpC22::Tn10) (pMC9)) were obtained from the American Type Culture Collection.

Isolation of DNA

The isolation of E. tenella chromosomal DNA, of chicken DNA and of E. coli DNA was performed as described by Clarke et al. Mol. Biochem. Parasitol., 22: 79–87; 1987.

Construction of Genomic Library

E. tenella DNA was partially digested with Eco RI (Bethesda Research Laboratories) and ligated with Eco RI digested, calf intestinal phosphatase (Boehringer Mannheim) treated, λamp3 using T4 DNA ligase (Boehringer Mannheim) at 4° C. for 16 hours. The final ligation volume for 1 μg DNA was 10 μl and the vector:insert ratio was 4:1. λamp3 was developed from λgt11 by Kemp et al. (P.N.A.S. USA 80:3787; 1983). Phage were packaged in vitro (Maniatis et al., Cold Spring Harbor Laboratory "Molecular Cloning: A Laboratory Manual"; 1982), incubated with E. coli strain Y1088 and plated in the presence of X-gal (5-bromo-4-chloro-3-indolyl-β-D-galactopyranoside) and IPTG (isopropyl-β-D-thiogalactopyranoside) (Bachem). This library was amplified (Maniatis et al., ibid.) and titered before screening.

Immunological Screening of Genomic Library and Preparation of Antisera

Performed as described by Clarke et al. (ibid).

B. Results

The recombinant bacteriophage EtHL6 contains a 722 bp EcoRI restriction fragment of E. tenella DNA. See also FIG. 7. Plaques generated by EtHL6 were originally identified as antibody-positive following screening of the genomic DNA library with immune chicken serum.

Example 7

Characterization of EtHL6 Fusion Protein

A. Methods

Affinity Selection of Antibody

Bacteriophage ($1×10^4$) from an EtHL6 stock were plated on E. coli strain Y1090 in 9 cm dishes and incubated at 42° C. for 3 hours. Each side of a filter, previously treated with IPTG as before, was placed in contact with the surface of the plate at 37° C. for 2 hours. Filters were incubated at room temperature for 1 hour with immune chicken serum (pre-absorbed with E.coli and diluted 1:20 in PBS pH 7.0 with 1% BSA). After washing, bound antibody was eluted with 5 ml 0.2 mol/l glycine (pH 2.8) for 10 minutes then neutralised with 650 μl of a solution comprising 2 mol/l Tris (80 μl); 10×PBS (500 μl); 2 mg/ml chloramphenicol (50 μl) and 0.25 g BSA. The selected antibody was used, without further dilution, to probe Western blots of sporozoite and merozoite proteins.

Fusion Proteins

E. coli strain Y1089 was lysogenised with phage described under Example 6B and lysates were prepared from 1 ml log phase cultures (Coppel et al., Nature 306: 751–756; 1983).

Polyacrylamide Gel Electrophoresis (PAGE)

Washed sporozoite pellets or solubilised phage lysates were solubilised in 2% (w/v) sodium dodecyl sulphate; 6 mol/l urea; 5% (v/v) 2-mercaptoethanol; 0.49 mol/l Tris-HCl; pH 6.7 with boiling for 5 min. After spinning for 5 min. in a microfuge, 50% (v/v) glycerol containing 0.1% (w/v) bromophenol blue was added to the supernates. The gels were discontinuous, with a 3.6% (w/v) acrylamide spacer gel, pH 6.7 and a 6–14% (w/v) acrylamide gradient resolving gel, pH 8.9 (16×0.1 cm). Electrophoresis was carried out at 50–70 V (constant voltage) for 16 h. and the bands were stained for protein with 0.2% (w/v) PAGE blue 83 (BDH chemicals) in 35% (v/v) methanol, 10% (v/v) acetic acid.

Immuno-Blotting of Polypeptides

After SDS-PAGE the slab gel was equilibrated for 30 minutes in 500 ml of 25 mmol/l Tris; 192 mmol/l glycine; pH 8.3; 20% (v/v) methanol (transfer buffer). Polypeptides in the gel were transferred electrophoretically to nitrocellulose paper (Towbin et al., PNAS 76: 4350–4354; 1979) (Schleicher & Schull, BA85, 0.45 μm) in a Transblot transfer cell (Bio-Rad Laboratories). Electrophoresis was carried out using transfer buffer at 4° C. for 16–22 hours at 30 V constant voltage. After transfer the nitrocellulose paper containing the sporozoite samples was blocked in PBS pH 7.0 containing 3% (w/v) bovine serum albumin (BSA; Sigma A4503). The strips of nitrocellulose containing the transferred marker protein were stained with Indian ink. Blots were reacted with immune or normal chicken serum (1:200 dilution in 1% (w/v) BSA; PBS; pH 7.0; 0.05% (v/v) Tween 20) for 1 hour at room temperature. The blots were washed 5 times for 5 minutes each time, in PBS; pH 7.0; 0.05% Tween 20 before incubation for 1 hour at room temperature with affinity-purified rabbit anti-chicken IgG (H+L)-peroxidase conjugate (Zymed Laboratories Inc.; 1:200 dilution in 1% (w/v) BSA; PBS; pH 7.0; 0.05% Tween 20). The blots were then washed a further 5 times as described above. Binding of the peroxidase conjugate was detected by reacting the nitrocellulose in 0.5 mg/ml diamino-benzidine; 50 mmol/l Tris-HCl pH 7.4; 200 mmol/l NaCl and 0.03% (v/v) $H_2O_2$. The reaction was stopped by washing the blot in PBS pH 7.0, 0.05% Tween 20.

B. Results

SDS-PAGE and Western blot analysis of the β-galactosidase fusion protein produced by EtHL6 confirmed its reaction with immune serum and also with mouse anti-β-galactosidase serum. The size of the polypeptide encoded by the eimeria DNA has been estimated as 35.5 kD (mean of two readings, data not presented).

Figure 4A:
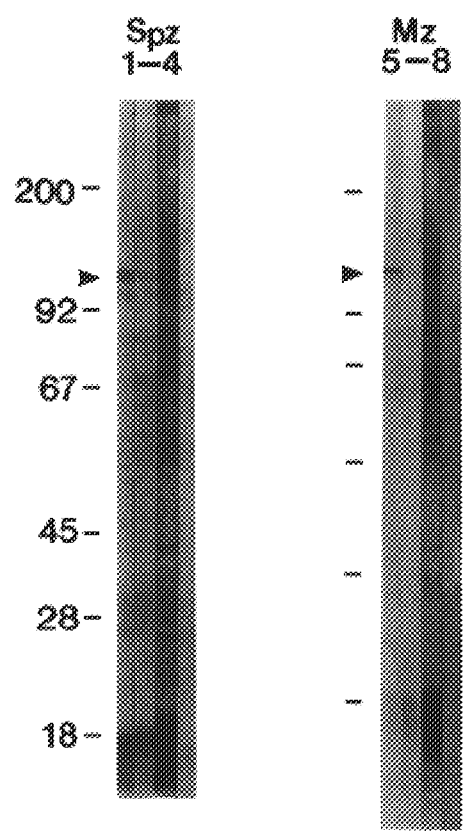
Figure 4B:
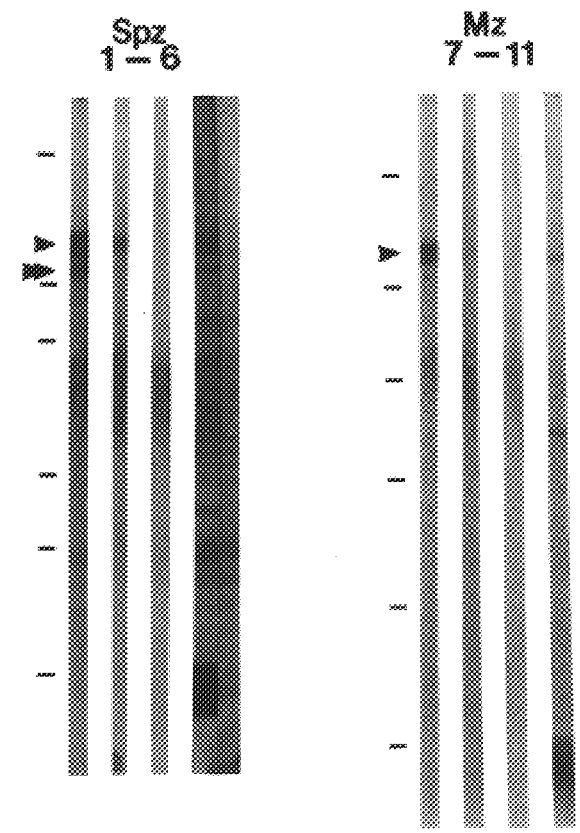

The native proteins corresponding to the EtHL6 antigen were identified using antibodies either raised in mice or in rabbits by injection of polyacrylamide gel slices containing the EtHL6 fusion protein or affinity purified from immune chicken serum. These antibodies reacted strongly with a polypeptide doublet of 110.0+1.0 kD (mean±S.E.M., n=12) on Western blots of proteins isolated from both sporozoites and second-generation merozoites of E. tenella (FIG. 4, single arrowheads). A weaker reaction with a third sporozoite polypeptide of 94.0±1.0 kD (n=5) is apparent in FIG. 4 (double arrowhead). A similar polypeptide has been identified in merozoites.

The mouse antiserum to the EtHL6 fusion protein also reacted with small groups of polypeptides on Western blots of proteins of E. maxima and E. acervulina sporozoites (FIG. 5). The molecular weights of the polypeptides were similar to those reacting on Western blots of E. tenella proteins, ranging from 108 to 92 kD for E. maxima and from 102 to 94 kD for E. acervulina.

Example 8

Characterization of EtHL6 Related DNA Sequences

A. Methods

Analysis of DNA

Phage stocks were prepared and DNA extracted from plate lysates. Plasmid and cosmid DNA was purified using standard techniques. (Maniatis et al. ibid.). After digestion with restriction endonucleases in the presence of 50 µg/ml RNase, DNA was fractionated on agarose gels in 40 mmol/l Tris-HCl, 20 mmol/l sodium acetate, 0.1 mmol/l EDTA (pH 8.3) (TAE buffer).

DNA Hybridisations

Restriction digests of genomic, phage, cosmid and plasmid DNA were fractionated on 1% agarose gels and transferred to Genescreen (New England Nuclear) in 25 mmol/l phosphate buffer pH 6.5 by the procedure of Southern (J.Mol.Biol. 98: 503–517; 1975). Hybridisation with DNA probes, $^{32}$P-labelled with a nick translation kit according to the manufacturer's instructions (Amersham), was at 37° C. for 16 hours in 1×Denhardt's solution, 0.1% (w/v) SDS and 4×saline sodium citrate (SSC). Colony hybridisations were carried out by the procedure of Grunstein and Hogness (P.N.A.S. USA 72: 3961–3965; 1975).

The DNA insert from clone EtHL6 was purified by electroelution (Maniatis et al., ibid.) from a 1% agarose gel in 40 mmol/l Tris-HCl; 20 mmol/l sodium acetate; 0.1 mmol/l EDTA; pH 8.3.

Autoradiography was carried out at −70° C. using Dupont intensifying screens and Fuji RX X-ray film.

Construction and Screening of a Cosmid Library of E. tenella Genomic DNA

E. tenella genomic DNA was partially digested with Mbo I, ligated with Bam HI digested cosmid pHC79 and packaged according to Maniatis et al. (ibid.). Approximately 500 colonies from the unamplified library were screened by probing with nick-translated purified EtHL6 insert. The cosmid clone 7.46 (the insert designated as Etg100—see also FIG. 7) was digested with a number of different restriction endonucleases, the fragments separated on agarose gels, Southern blotted onto nitrocellulose, and probed again to identify restriction fragments containing the EtHL6 related sequences.

Screening of E. tenella cDNA Library in αgt10 cDNA clones of sporulated E. tenella oocyst mRNA in λgt10 were screened by probing with the nick-translated purified EtHL6 insert described above. Twenty-one positive phages were found. One of these (cDNA 10—the insert designated as Etc100—see also FIG. 7) was chosen for further study.

Sequencing of Clones

The inserts from EtHL6 and EtHL6 related clones (cosmid Etg100 and Etc100) were subcloned into either M13mp, pUC13 or pAT153 derived vectors prior to sequencing. Sequencing reactions were carried out by the dideoxy method (Bankier & Barrell, Techniques in the Life Sciences (Biochemistry) 85: Techniques in Nucl. Acids Bioch. 1–34; 1983).

B. Results

Physical mapping of DNA from EtHL6 indicated that the size of the EcoRI insert was approximately 700 bp and that it contained a single HindIII site. Nucleotide sequence analysis established the exact size of the insert to be 722 bp and confirmed the presence of a HindIII site close to one end of the insert. The reading frame was established with reference to the known reading frame of the EcoRI cloning site in the λamp3 vector which would result in the production of a fusion protein. The only large open reading frame (ORF) identified was in the orientation that placed the HindIII site in the distal portion of the insert relative to the β-galactosidase gene. Restriction mapping of EtHL6 bacteriophage DNA confirmed that this was indeed the active orientation.

Since the EtHL6 fragment does not contain the entire gene a cosmid library of partially digested E. tenella genomic DNA was screened and a recombinant cosmid 7.46 isolated. Southern blotting of various restriction enzyme digests of this cosmid revealed two HindIII fragments of approximately 3 kb and 1.3 kb which hybridised to the probe. A further 1.7 kb HindIII fragment was identified which lies 3' to the 1.3 kb HindIII fragment. The 3 kb HindIII (H3), 1.3 kb HindIII (H3A), 1.35 EcoRI (E5) and 1.7 kb HindIII (C4) fragments were subcloned into pUC 13 and their nucleotide sequences determined to give 5,990 bp of contiguous genomic sequence with the EtHL6 fragment extending from position 2359 to 3080. This nucleotide sequence is shown in FIG. 6.

In addition to genomic sequencing, the sequence of one cDNA clone from a λgt10 library, cDNA10 identified by hybridisation to the EtHL6 insert, was determined. The insert is 3,402 bp long, begins at position 688 on the genomic sequence and finishes at position 4,993 with three intervening non-coding regions (introns) identified in the genomic sequence. The sequence data obtained from this cDNA clone matches to the genomic sequence is indicated in FIG. 6. There is an additional sequence of A(17) at the 3' end of Etc100, representing the poly A tail of Etc100.

Aligning of EtHL6—Related Sequences

FIG. 7 shows the allignments of EtHL6, Etg100, Etc100 and Et100.

The positions of the ends of Etc100 are indicated on FIG. 6 along with the predicted amino acid sequence and the genomic introns. Etc100 does not appear to be coding for the whole of its length. At the 5' end there is a single termination codon at nucleotides 9–11 (TAG, nucleotides 696–698 of the genomic sequence of FIG. 6) followed immediately in the same reading frame by predicted coding sequence which has its first potential initiation codon at nucleotides 78–80 (ATG, nucleotides 765–767 of the genomic sequence of FIG. 6) and continues uninterrupted to nucleotide 2213 (nucleotide 3804 of the genomic sequence of FIG. 6) where it is followed by an in frame termination codon (TAA). This is followed by 1,189 bp of apparently non-coding sequence before the 3' terminus.

The polypeptide predicted by this open reading frame is 712 amino acids in length with a calculated molecular weight of 74.8 kD. The predicted amino acid sequence is shown in FIG. 8 along with a table of the sequence composition. This sequence was analyzed for possible antibody binding epitopes using the algorithms of Hopp and Woods (ibid.) and Chou and Fassman (ibid.) resulting in the following epitope regions: 270–300 and 495–525.

Example 9

Construction of a Fowlpoxvirus Recombinant Expressing Et100

A) Plasmid Construction

1 μg of plasmid p1019, which contains all of Etc100 except the 362 nucleotides at the 3' end, was cut with restriction enzymes BamHI and HindIII. The Etc100 BamHI/HindIII fragment contains the BamHI to EcoRI portion of the puC13 polylinker upstream of the 5'non-coding sequence and the predicted open reading frame and ends at the HindIII site within the 3' non-coding region (position 4309–4314 on FIG. 6*c*). The restriction digest was end-repaired with 10 units T4-DNA polymerase and 10 units *E.coli* DNA polymerase (large fragment) then cloned into a blunt-ended insertion site in a fowlpoxvirus recombinant plasmid. Bacterial colonies containing plasmids with the Etc100 insert were identified by probing with $^{32}P$-labelled Etc100 and the orientation of the inserts determined by restriction digestion of mini-prepped DNA. A plasmid which contained the insert in the correct orientation for expression in fowlpoxvirus was identified. An oligonucleotide, which is complementary to a region just within the Etc100 predicted open reading frame (nucleotides 788–802 on FIG. 6*a*), was used as a primer to sequence the junction of the Etc100 sequence and the fowlpoxvirus recombination plasmid direct from plasmid DNA. This sequencing confirmed that the Etc100 BamHI/HindIII fragment was adjacent to and in the correct orientation with the fowlpoxvirus transcriptional promoter of the vector.

B) Recombinant into Fowlpoxvirus

Plasmid was transfected into chick embryo fibroblasts (CEFS), infected with fowlpoxvirus, strain FP9, using standard calcium phosphate techniques. Recombinant viruses were isolated and plaque purified three times. One recombinant virus, called fowlpoxvirus E10, was used for further study. A master stock of E10 was obtained by inoculating a 25 $cm^2$ flask with virus from a single plaque and storing the resultant virus in aliquots at −20° C. Sub-master stocks were obtained by inoculating batches of 20 125 $cm^2$ flasks with 0.1 plaque-forming units (p.f.u.) per cell of master stock. All stocks were titred by plaquing on CEFs using standard techniques.

C) Expression of Et100 by Fowlpoxvirus E10

Sub-confluent monolayers of CEFs in 25 $cm^2$ or 125 $cm^2$ flasks were infected with fowlpoxvirus E10 at 0.1 p.f.u. per cell. Infected cells were harvested at various times post-infection by scraping into phosphate buffered saline pH 7.0 and lysed by the addition of an equal volume of 2×Laemmli buffer. Lysates (equivalent of approximately $10^6$ infected cells) were boiled for five minutes then loaded onto 10% polyacrylamide gels and electrophoresed overnight at 100 v. Equivalent lysates from cells infected with parental fowlpoxvirus were run alongside. Gels were electroblotted onto nitrocellulose using standard techniques and the nitrocellulose membrane probed with antisera to *Eimeria tenella*. In the lysates from E10, a polypeptide of around 100 kD in size was recognised by rabbit anti-sporozoite and chicken convalescent antisera. This polypeptide was not present in the lysates from cells infected with parental fowlpoxvirus. The 100 kD polypeptide was detected at 2 days post infection using a multiplicity of infection of 0.1 p.f.u. and persisted until 7 days at which time the monolayers were completely destroyed by virus cytopathic effects. The polypeptide was detected on both reducing and non-reducing gels.

D) Vaccination with Et100 Expressing Fowlpoxvirus E10

1) Groups of three week old birds (Light Sussex) were inoculated intravenously with $3\times10^7$ p.f.u. of parental fowlpoxvirus (Group I) or recombinant fowlpoxvirus E10 (Group II) made up in 500 μl of 199 tissue culture medium. A third group were inoculated with the 199 medium alone (Group III). All birds received a second identical injection at five weeks of age and ten days after the booster they were all bled. ELISA titres against both fowlpoxvirus and *Eimeria tenella* smashed sporulated oocysts were determined. Over 90% of birds from both virus inoculated groups had antibodies to fowlpoxvirus which titred out to beyond 1 in 64,000 whereas birds in the control group had negligeble titres. The titres to *Eimeria tenella* were not significantly raised but at a dilution of 1 in 1,000 the optical density readings were slightly raised in the E10 group (see below for example).

ELISA readings at 1 in 1,000 dilution of antisera

| Group | anti-FPV(mean) | Anti-E.t(mean) |
|---|---|---|
| I | 0.844 | 0.126 |
| II | 0.855 | 0.161 |
| III | 0.016 | 0.070 |

Antisera from each group of ten birds was pooled and used to probe Western blots of electrophoretically separated proteins from *Eimeria tenella* sporozoites or second generation merozoites. At serum dilutions of 1 in 1000 the pooled antisera from birds inoculated with recombinant E10 recognised the Et100 polypeptide on both sporozoites and merozoites whereas sera from the other groups did not.

2) Groups of one week old birds were inoculated by scarification of the wing-web with $3\times10^6$ p.f.u. of either parental or recombinant fowlpoxvirus E10 made up in 50 μl of 199 tissue culture medium. A third group of birds were inoculated with 199 medium only. At four weeks of age all the birds were given a second inoculation, but this time with $3\times10^7$ p.f.u. of the appropriate virus again in 50 μl of 199 medium. From four weeks onwards all birds were bled at weekly intervals and the sera used to probe Western blots of electrophoretically separated proteins from *Eimeria tenella* sporozoites and second generation merozoites. No reactivity was seen at four weeks but by one week later (1 week after de second inoculation) the birds receiving E10 specifically recognised Et100 from both sporozoites and merozoites.

BRIEF DESCRIPTION OF THE DRAWINGS

FIG. 1A & B

Western blots of *E. tenella* sporozoites and $2^{nd}$ generation merozoites probed with monoclonal antibodies.

A. Sporozoite blot probed with

E. TEN 10Y-2 (lane 1), E. TEN 11P-2 (lane 2)

B. Merozoite blot probed with

E. TEN 10Y-2 (lane 1), E. TEN 11P-2 (lane 2).

FIG. 2

Expression of Etp100 (arrow) in different sporogonic stages. Western blot of SDS-PAGE separated material of different stages probed with hyperimmune chicken serum lane 1: sporulated oocysts lane 2: sporocysts lane 3: sporozoites

FIG. 3A AND B

Immunoaffinity purification of Etp100 (arrow) from *E. tenella* sporocysts using E. TEN 11P-2 or E. TEN 10Y-2 monoclonal antibodies.

A. Silver-stained SDS-PAGE of glycine/HCl (pH 2.6) eluted fractions and starting material
lane 1: eluted from E. TEN 10Y-2 column
lane 2: eluted from E. TEN 11)-2 column
lane 3: starting material B. Western blot of starting material and pH 2.6 eluted fractions probed with polyclonal rabbit anti-sporozoite serum
lane 1: starting material
lane 2: eluted from E. TEN 11P-2 column
lane 3: eluted from E. TEN 10Y-2 column

FIG. 4A and B

Identification of the native proteins corresponding to the EtHL6 antigen.

Panel A. Antibodies selected with protein from plaques generated by the recombinant bacteriophage EtHL6 (lanes 1 and 5) and λamp3 (negative control; lanes 2 and 6), immune chicken serum (lanes 3 and 7) and normal chicken serum (lanes 4 and 8) were used to probe Western blots of reduced proteins from E. tenella sporozoite (spz) and merozoite (Mz) proteins.

Panel B. Antisera raised to the EtHL6 fusion protein.

Mouse anti-EtHL6 fusion protein (lanes 1 and 7), rabbit anti-EtHL6 fusion protein (lanes 2 and 8), rabbit antiserum raised against proteins produced by a λamp3 lysogen migrating on an SDS-PAGE gel in the same region as the EtHL6 fusion protein (negative control; lanes 3 and 9), normal rabbit serum (lanes 4 and 10), immune chicken serum (lane 5) normal chicken serum (lane 6) and antiserum raised in rabbits against E. tenella sporozoites (lane 11) were used to probe Western blots of reduced proteins from E. tenella sporozoites (Spz) and/or merozoite (Mz) proteins.

The single arrowheads indicate the position of the polypeptide doublet of 110 and 102 kD; the position of a third polypeptide of 94 kD is illustrated by the double arrowheads (see text for further details). The molecular weight markers were myosin, 200 kD; phosphorylase, 92 kD; bovine serum albumin, 67 kD; ovalbumin, 45 kD; carbonic anhydrase, 28 kD and myoglobin, 19 kD.

FIG. 5

Detection of native polypeptides from heterologous species corresponding to the EtHL6 antigen.

Mouse antisera raised against the EtHL6 fusion protein (lanes 1, 3 and 5) and proteins produced by a λamp3 lysogen migrating in the same region on an SDS-PAGE gel as the EtHL6 fusion protein (negative control, lanes 2, 4 and 6) were reacted with Western blots of reduced proteins from sporozoites of E. tenella (lanes 1 and 2, E. maxima (lanes 3 and 4) and E. acervulina (lanes 5 and 6). The positions of the molecular weight markers are indicated.

FIG. 6A–H

The nucleotide sequence of E. tenella genomic DNA (Etg100), extends from nucleotides 1 to 5990. The genomic insert from EtHL6 corresponds to nucleotides 2359 to 3080. The translated amino acid sequence shown is that predicted from Etc100. Three genomic introns are indicated by dashed regions and the 5' and 3' ends of Etc100 are indicated by solid dots.

FIG. 7

Schematic allignment of EtHL6 and EtHL6-related genomic and cDNA sequences.

The 5' and 3' ends are indicated by solid dots. The three genomic introns are indicated by dashed regions.

FIG. 8

The predicted amino acid sequences of Etp100 and a statistical analysis of the content.

We claim:

1. An isolated protein which is an *Eimeria tenella* antigen, wherein said protein has an apparent molecular weight of about 100±10 kD in SDS-PAGE and binds to monoclonal antibody Et11P-2 under non-reducing conditions but not under reducing conditions and occurs in the sporulated oocyst, sporocyst, sporozoite, first and second generation schizonts and second generation merozoite of *Eimeria tenella*.

2. The protein of claim 1, comprising the amino acid sequence depicted in FIG. 8.

3. A vaccine having protective activity against Eimeria infection, comprising an immunogenic amount of the protein of claim 1, and a pharmaceutically acceptable excipient.

4. A polypeptide consisting of the amino acid sequence ISPQKPGSPPCPTCEAPRGRSCAEQPPGLTR.

5. A method for isolating the protein of claim 1, said method comprising immune-adsorbing an extract of an Eimeria species using a column substrate which contains monoclonal antibody Et11P-2 and separating the adsorbed fraction of the extract from the unadsorbed fraction, and subsequently releasing the adsorbed fraction from the column substrate, whereby the protein is obtained.

* * * * *